United States Patent
Polymeropoulos

(10) Patent No.: US 10,821,099 B2
(45) Date of Patent: *Nov. 3, 2020

(54) USE OF TRADIPITANT IN MOTION SICKNESS

(71) Applicant: Vanda Pharmaceuticals Inc., Washington, DC (US)

(72) Inventor: Mihael H. Polymeropoulos, Potomac, MD (US)

(73) Assignee: Vanda Pharmaceuticals Inc., Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/591,927

(22) Filed: Oct. 3, 2019

(65) Prior Publication Data

US 2020/0101045 A1 Apr. 2, 2020

Related U.S. Application Data

(63) Continuation of application No. PCT/US2019/053107, filed on Sep. 26, 2019.

(60) Provisional application No. 62/874,927, filed on Jul. 16, 2019, provisional application No. 62/737,992, filed on Sep. 28, 2018.

(51) Int. Cl.
*A61K 31/4192* (2006.01)
*A61P 1/08* (2006.01)

(52) U.S. Cl.
CPC ............ *A61K 31/4192* (2013.01); *A61P 1/08* (2018.01)

(58) Field of Classification Search
CPC .............................. A61K 31/4192; A61P 1/08
See application file for complete search history.

(56) References Cited

U.S. PATENT DOCUMENTS

| 6,140,324 A * | 10/2000 | Tattersall ............... A61K 31/14 514/226.2 |
| 6,297,375 B1 | 10/2001 | Bös et al. |
| 7,320,994 B2 | 1/2008 | Amegadzie et al. |
| 7,381,826 B2 | 6/2008 | Borghese et al. |
| 8,772,496 B2 | 7/2014 | Chen |
| 10,463,655 B2 | 11/2019 | Polymeropoulos et al. |
| 2015/0320866 A1 * | 11/2015 | Ottoboni ............... A61K 47/34 514/93 |
| 2016/0136162 A1 | 5/2016 | Trento et al. |
| 2018/0110761 A1 | 4/2018 | Polymeropoulos et al. |

FOREIGN PATENT DOCUMENTS

| EP | 1501809 B1 | 1/2008 |
| WO | 2019099883 A1 | 5/2019 |

OTHER PUBLICATIONS

Warr, David G., et al.; "Evaluation of risk factors predictive of nausea and vomiting with current standard-of-care antiemetic treatment: analysis of phase 3 trial of aprepitant in patients receiving adriamycin-cyclophosphamide-based chemotherapy"; SpringerLink; Jun. 2011, vol. 19; Issue 6; pp. 807-813.

Pasricha, Pankaj J., et al.; Aprepitant Has Mixed Effects on Nausea and Reduces Other Symptoms in Patients with Gastroparesis and Related Disorders; Gastroenterology; Jan. 2018; vol. 154, Issue 1; pp. 65-76.

International Search Report and Written Opinion for corresponding PCT Application No. PCT/US2019/053107 dated Dec. 5, 2019, 19 pages.

* cited by examiner

*Primary Examiner* — Sarah Pihonak
(74) *Attorney, Agent, or Firm* — Hoffman Warnick LLC

(57) ABSTRACT

Disclosed herein is a method of treating or preventing motion sickness or at least one symptom thereof, comprising treatment with the NK-1 receptor antagonist, tradipitant.

20 Claims, 6 Drawing Sheets

Reversal of NK-1 agonist-induced foot-tapping behavior in gerbils by tradipitant and competitor NK-1 antagonists: dose response

* = $p < 0.05$ vs. vehicle

■ Aprepitant (ED$_{50}$ = 0.4 ± 0.05 mg/kg, n=4-10, 1 hr.)

▽ CP-122721 (ED$_{50}$ = 2.2 ± 0.5 mg/kg, n=6-8, 0.5 hr.)

● Tradipitant (ED$_{50}$ = 0.03 ± 0.004 mg/kg, n=6-7, 2 hrs.)

Reversal of NK-1 agonist-induced foot-tapping behavior in gerbils by tradipitant and competitor NK-1 antagonists: Time course (p.o.; n=5-13)

Effect of tradipitant on NK-1 agonist (GR73632)-induced vocalization in guinea pigs: tradipitant concentration range of 0.05 – 10 mg/kg Duration of activity: suppression by tradipitant (0.1 mg/kg) of NK-1 agonist (GR73632)-induced vocalization in guinea pigs Vehicle = 10% ethanol/emulphor, 10% propylene glycol

USE OF TRADIPITANT IN MOTION SICKNESS

CROSS REFERENCE TO RELATED APPLICATIONS

The present application is a continuation of International Application No. PCT/US19/53107, filed Sep. 26, 2019, which claims the benefit of U.S. Provisional Application No. 62/737,992, filed Sep. 28, 2018, and U.S. Provisional Application No. 62/874,927, filed Jul. 16, 2019.

BACKGROUND

The application relates generally to the use of NK-1 receptor antagonists. More particularly, the application relates the use of the NK-1 antagonist, tradipitant in motion sickness.

Motion sickness is a disorder defined by a constellation of symptoms that can result from real or perceived sickness-inducing motion. Such motion may include, e.g., motion involving the head of a subject that can produce one or more symptoms characteristic of motion sickness. The sickness-inducing motion that gives rise to motion sickness may commonly include riding in any form of transportation such as, e.g., automobiles, buses, trains, other ground or rail transportation, boats under power, ferries, cruise ships, sailboats, personal water craft, canoes, kayaks, row boats, airplanes and helicopters, amusement rides, and certain gymnastic maneuvers such as somersaults. The symptoms of motion sickness typically can include, but are not limited to, nausea, vomiting, dizziness, headache, fullness, cold sweats, sweating, pallor, disorientation, and anorexia. Motion sickness has been reported to affect up to 30% of the general population under ordinary travel conditions that include sea, air, and land travel. The prevalence of motion sickness in one epidemiological study during bus travel found 28% of passengers reporting feeling ill while 13% reported experiencing nausea.

Under the sensory conflict theory, motion sickness is described as arising due to a mismatch between the perceptions of motion, or lack thereof, by the visual, vestibular, and somatosensory systems. A discrepancy between actual body position and perceived body position is believed to trigger the maladaptive response of motion sickness. Motion sickness is one of the most prevalent episodic disorders in the world, and its prevalence has dramatically increased with world population mobility. Despite the increasing prevalence of the disorder, the treatments available today, which are primarily antihistamines and anticholinergics, were first discovered in the 1940's.

The mammalian tachykinins (neurokinins [NKs]) are a family of peptide neurotransmitters that share a common C-terminal sequence. This group includes substance P (SP), neurokinin-A (NKA), and neurokinin-B (NKB). SP, the most abundant NK, preferentially binds to the neurokinin type-1 (NK-1) receptor and is involved in the regulation of many physiological processes. NK-1 receptors have been mapped in the central nervous system and were found to have a broad distribution in the brain, including the midbrain, basal ganglia, hypothalamus, and limbic system. Neurokinin receptors are also widely distributed in the gut, the bronchial tree, and the vascular system.

The NK-1 receptor has been identified as a potential therapeutic target for the treatment of motion sickness. Maropitant, another neurokinin 1 receptor antagonist, is approved for the prevention of vomiting due to motion sickness in dogs and cats. A crossover study showed that the therapy reduced the occurrence of vomiting in over 75% of dogs as compared to placebo. This data supports the exploration of the effects of NK-1 antagonists on motion sickness in humans, though maropitant has a different molecular composition and pharmacokinetics from other NK-1 antagonists. Another NK1-receptor antagonist, aprepitant, is approved for postoperative nausea and vomiting (PONV) in adults, and for use with other medications in children and adults to prevent nausea and vomiting caused by certain anti-cancer (chemotherapy) medicines. Currently, tradipitant is being tested in clinical trials for the treatment of nausea and vomiting in patients with gastroparesis. Currently, available therapies are not effective for all patients and some of the medications used have significant side effect profiles.

Tradipitant is a highly potent, selective, centrally penetrating, and orally active neurokinin-1 (NK-1) receptor antagonist, depicted below as the compound of Formula (I)

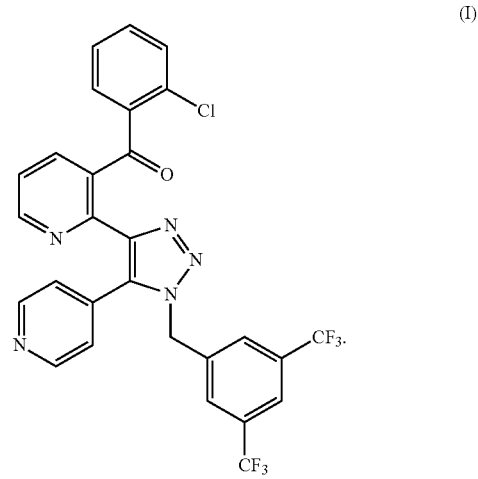 [SMILES: O=C(c1ccccc1Cl)c1cccnc1-c1nnn(Cc2cc(C(F)(F)F)cc(C(F)(F)F)c2)c1-c1ccncc1]

Tradipitant is disclosed in U.S. Pat. No. 7,320,994, and contains six main structural components: the 3,5-bis-trifluoromethylphenyl moiety, two pyridine rings, the triazol ring, the chlorophenyl ring, and the methanone. Tradipitant is known by the chemical names: 2-[1-[[3,5-bis(trifluoromethyl)phenyl]methyl]-5-(4-pyridinyl)-1H-1,2,3-triazol-4-yl]-3-pyridinyl](2-chlorophenyl)-methanone, and {2-[1-(3,5-bistrifluoromethylbenzyl)-5-pyridin-4-yl-1H-[1,2,3]triazol-4-yl]-pyridin-3-yl}-(2-chlorophenyl)-methanone, and has also been known as LY686017 and as VLY-686. Crystalline Forms IV and V of tradipitant are disclosed in U.S. Pat. No. 7,381,826, and a process for preparing crystalline {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV is disclosed in U.S. Pat. Nos. 8,772,496; 9,708,291; and 10,035,787.

In preclinical and clinical studies, tradipitant produces a long-lasting blockade of brain NK-1 receptors. Although the distinct pathways of nausea and vomiting are largely undetermined, a definitive role of SP acting at NK-1 receptors in the nucleus tractus solitarus has been confirmed. Previous clinical studies have demonstrated the efficacy of NK-1 antagonism in the prevention of chemotherapy induced and post-operative nausea and vomiting (CINV and PONV).

BRIEF DESCRIPTION OF THE INVENTION

A first aspect of the invention provides a method of prevention of motion sickness or one or more symptoms thereof, in an individual anticipating experiencing sickness-inducing motion, comprising administering tradipitant to said individual in an amount effective to prevent manifestation of motion sickness or one or more symptoms thereof.

In practicing the foregoing method, the amount of tradipitant that is effective to prevent motion sickness or a symptom thereof may be, e.g., 100-400 mg, 100-300 mg, or 100-200 mg. For example, the effective amount can be about 170 mg. The effective amount may be administered in a single dose, such as a single oral dose, and may or may not be in a single dosage unit form. The dose may be administered in advance of engaging in a sickness-inducing motion, typically about 30 minutes before commencing such motion. Administration of such an effective amount prior to commencing sickness-inducing motion can prevent or reduce the severity or frequency of one or more symptoms of motion sickness, including the prevention of nausea, vomiting, dizziness, headache, fullness, cold sweats, sweating, pallor, or disorientation.

A second aspect of the invention provides a method of treating motion sickness or one or more symptoms thereof, in an individual experiencing the manifestation of motion sickness, comprising administering tradipitant to said individual in an amount effective to treat the motion sickness or the symptom thereof. Treatment of motion sickness may be considered to include a reduction in severity of symptoms, the prevention of progression, or the complete resolution of one or more symptoms of motion sickness after such symptom or symptoms have manifest in the individual. In practicing the foregoing method, the amount of tradipitant that is effective to treat motion sickness or a symptom thereof may be, e.g., 100-400 mg, 100-300 mg, or 100-200 mg. For example, the effective amount can be about 170 mg. The effective amount may be administered in a single dose, such as a single oral dose, and may or may not be in a single dosage unit form. The dose may be administered after the onset of at least one symptom of motion sickness, preferably soon after the onset of the at least one symptom, and more preferably, immediately after the onset of the at least one symptom. Administration of such an effective amount after motion sickness has begun to manifest can reduce the severity of the symptom(s), eliminate the symptom(s), prevent the progression or intensification of the symptom(s) of motion sickness, for example from dizziness to nausea, from nausea to vomiting, etc.

A third aspect of the invention provides tradipitant for use in any of the methods of treatment or prevention described in the preceding aspects.

A fourth aspect of the invention provides a pharmaceutical composition comprising tradipitant for use in any of the preceding methods of treatment or prevention.

A fifth aspect of the invention provides tradipitant for use in the manufacture of a pharmaceutical composition comprising tradipitant for use in any of the preceding methods of treatment or prevention.

These and other aspects, advantages and salient features of the invention will become apparent from the following detailed description, which, when taken in conjunction with the annexed figure(s) disclose embodiments of the invention.

Figure 1:
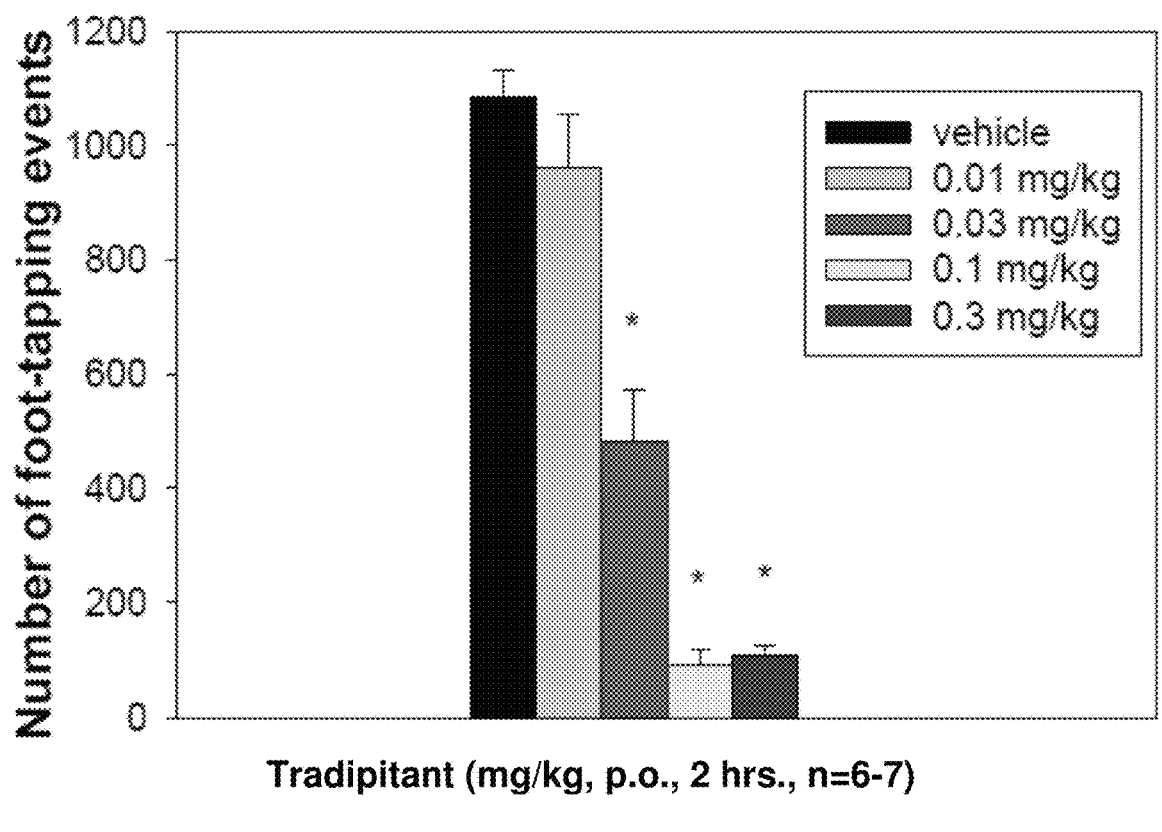
FIG. 1 illustrates the effect of tradipitant on NK-1 agonist (GR73632, 3 pmol, icv)-induced foot-tapping behavior after oral administration.

The drawings are intended to depict only typical aspects of the disclosure, and therefore should not be considered as limiting the scope of the disclosure.

DETAILED DESCRIPTION OF THE INVENTION

The method of using tradipitant as described herein requires administering an amount of tradipitant that is effective to prevent or treat motion sickness or a symptom thereof. The amount administered to a subject being treated depends upon a number of factors, including the species being treated, the weight of the subject being treated, and the subject's condition otherwise. The method specifically involves the prevention and amelioration of motion sickness in human beings, including adult human beings. In adult human beings the typical dose effective to prevent motion sickness or a symptom thereof is 100-400 mg, 100-300 mg, or 100-200 mg. One specific regime involves administration of about 85-170 mg, or more particularly about 170 mg.

As used herein, the terms "patient," "subject," and "individual" refer to a mammal who is administrated tradipitant. Guinea pigs, dogs, cats, gerbils, horses, cattle, sheep, and humans are within the scope of the terms "patient," "subject," and "individual." The most preferred subject is a human being. The term "effective amount," i.e., dose, of tradipitant refers to an amount that is effective in treating or preventing the disorders described herein, or symptoms thereof.

As indicated above, a method is provided herein for preventing motion sickness or a symptom thereof, in an individual anticipating experiencing sickness-inducing motion. Such method comprises prophylactically administering tradipitant to said individual in an amount effective to prevent the manifestation of motion sickness or one or more symptoms thereof. The effective amount of tradipitant to prevent motion sickness or a symptom thereof may be, e.g., 100-400 mg, 100-300 mg, 100-200 mg, or 85-170 mg, and may particularly be about 170 mg. The effective amount may be administered in a single dose such as, e.g., a single oral dose, and may or may not be in a single dosage unit form. The dose may be administered in advance of engaging in a sickness-inducing motion, for example, in advance of boarding an airplane, train, boat, or other vehicle, or getting into an automobile, or before an anticipated airplane takeoff or commencement of motion on board any other type of vehicle. Particularly, the dose may be administered about thirty (30) minutes prior to commencement of the potentially motion sickness-inducing motion or activity. Such administration of an effective amount of tradipitant can prevent the manifestation of one or more symptoms of motion sickness, including the prevention of nausea, vomiting, dizziness, headache, fullness, or disorientation, or may limit the symptom(s) experienced by the individual and the severity thereof.

A method is also provided herein for treating motion sickness or a symptom thereof after such motion sickness has already manifest or begun to manifest in the individual. Such method includes administering tradipitant to said individual in an amount effective to treat the motion sickness or the symptom thereof. Treatment of motion sickness in the present context includes all processes in which there may be a slowing, interrupting, arresting, controlling, or stopping of the progression of motion sickness and/or symptoms thereof. For example, such treatment may include the prevention of progression, or the partial or complete resolution of one or more symptoms of motion sickness after such symptom or symptoms have manifest in the individual. In practicing the foregoing method, the amount of tradipitant that is effective to treat motion sickness or a symptom thereof may be, e.g., 100-400 mg, 100-300 mg, 100-200 mg, 85-170 mg, or particularly about 170 mg. The effective amount may be administered in a single dose, including a single oral dose, which may or may not be in a single dosage unit form. The effective amount of tradipitant may be administered after the onset of at least one symptom of motion sickness. Preferably, the effective amount is administered soon after the onset of the at least one symptom, for example up to thirty (30) minutes after the onset of the at least one symptom, and more preferably, the effective amount is administered immediately or substantially immediately after the onset of the at least one symptom. Administration of such an effective amount after motion sickness has begun to manifest can reduce the severity of the symptom(s), eliminate the symptom(s), or prevent the progression or intensification of the symptom(s) of motion sickness, for example from dizziness to nausea, from nausea to vomiting, etc.

The skilled artisan will appreciate that additional preferred embodiments may be selected by combining the preferred embodiments above, or by reference to the examples given herein.

EXAMPLES

Example 1

Pre-Clinical Studies

Tradipitant is a selective neurokinin-1 (NK-1) receptor antagonist. In vitro, tradipitant potently inhibits NK-1 receptor binding and antagonizes the effects of an NK-1 agonist in a functional assay. No significant activity is observed in a panel of 74 additional receptors, enzymes, and ion channels including the NK-2 and NK-3 receptors. By 3 different measures, tradipitant is also a potent centrally active NK-1 antagonist in vivo.

Example 1.1

Mechanism Studies

Tradipitant inhibits [$^{125}$I] substance P (SP) binding to the NK-1 receptor expressed by IM-9 cells with a $K_i$ of 0.062 nM and inhibits the SP-induced mobilization of intracellular calcium in U373 cells with a $K_b$ of 0.095 nM (Table 1).

TABLE 1

Affinity of tradipitant for NK-1 Receptors In Vitro

| Antagonist | IM-9 Human Cell Membrane Binding $K_i$ (nM) | Calcium Mobilization in U373 Cells $K_b$ (nM) |
|---|---|---|
| Tradipitant | 0.062 ± 0.012 | 0.095 ± 0.025 |
| Aprepitant | 0.14 ± 0.03 | 0.14 ± 0.01 |
| CP-122721 | 0.027 ± 0.01 | 0.034 ± 0.009 |

These potencies are similar to those observed with the NK-1 antagonists aprepitant (MK-869) and CP-122721. In addition, results from tradipitant evaluation in a panel of 74 other receptors, enzymes, and ion channels indicate that, at a test concentration of 1 μM, tradipitant does not exhibit any inhibition of binding greater than 50%. At the NK-2 and NK-3 receptors, the compound produces no significant inhibition. Therefore, tradipitant is a highly selective NK-1 antagonist in vitro.

As shown in Table 2, several of the major metabolites of tradipitant have an affinity for the NK-1 receptor based on a binding assay. These metabolites have high affinity for the NK-1 receptor.

TABLE 2

Affinity of tradipitant metabolites for NK-1 Receptors in vitro

| Metabolite | Designation | IM-9 Human Cell Membrane Binding $K_i$ (nM) |
|---|---|---|
| LSN2081070 | M2 (Racemic) | 0.09 (n = 1) |
| LSN2107355 | M2 (S-enantiomer) | 0.08 (n = 1) |
| LSN2107357 | M2 (R-enantiomer) | 0.94 (n = 1) |
| LSN2195411 | M3 | 0.03 (n = 1) |
| LSN2195413 | M4 (Racemic) | 0.08 (n = 1) |

Example 1.2

Efficacy Models for In Vivo Evaluation of Brain NK-1 Receptor Occupancy and Efficacy of Tradipitant Example 1.2.1

Effects of Tradipitant on Centrally Administered NK-1 Agonist-Induced Foot-Tapping Behavior in Gerbils Introduction Differences in species selectivity of NK-1 receptors pose challenges to characterization of NK-1 receptor antagonists in vivo. Gerbil NK-1 receptors have previously been shown to be similar to those in humans. Gerbils exhibit a characteristic stereotypic foot-tapping behavior in response to distress, fear, or aversive stimuli. Intracerebroventricular (icv) administration of substance P or a selective NK-1 receptor agonist such as GR73632 produces rapid rhythmic tapping of the hind feet lasting approximately 5 minutes, which can be inhibited by systemic administration of a brain penetrating antagonist of the NK-1 receptor. This response is selective for NK-1 agonists, since selective NK-2 and NK-3 agonists do not elicit a similar response. This behavioral response is further characterized and modified to enable identification and optimization, in vivo, of potent NK-1 receptor antagonists including tradipitant.

Methods

Male Mongolian gerbils (Harlan Sprague Dawley, Indianapolis, Ind.) weighing 26 to 40 grams are administered the selective neurokinin-1 receptor agonist GR73632 (3 pmol) via direct, vertical, free-hand intracerebroventricular (icv) injection to a depth of 4.5 mm below bregma with a cuffed 27-gauge needle attached to a 50 µl Hamilton syringe. Immediately after injection, animals are placed individually into isolated chambers with pressure-sensitive velocimeter platform floors (San Diego Instruments acoustic startle apparatus) that detect and quantify vibration. The San Diego Instruments "SR" DOS-based computer program is used on a PC to record the number of foot-taps over the following 6 to 10 minutes, beginning 30 seconds after the floor is lightly tapped. Raw data are converted with a Microsoft® Excel® (Microsoft® and Excel® are registered trademarks of Microsoft Corp., Redmond, Wash.) macro that determines the number of events over threshold (125) in each 250-millisecond time bin over the 5.5 minutes following onset of observation. The total number and average intensity of events over the duration is determined. Total number of taps is analyzed with one-way ANOVA and post-hoc Dunnett's test using JMP statistical software.

A dose-response curve (with doses of 0.3, 1, 3 and 10 pmols, icv) is initially generated with the NK-1 agonist GR73632. Maximal foot-tapping behavior is achieved with 3 and 10 pmol doses; the 3 pmol dose is subsequently chosen as the dose of choice for antagonism experiments.

NK-1 antagonists are tested for their ability to attenuate GR73632-induced foot tapping. NK-1 antagonists are administered (po) via oral feeding tube at doses and time points specified in each experiment. All animals receive only one dose of NK-1 antagonists in all tests.

$ED_{50}$ Determinations/Dose-Response Tests

NK-1 antagonists are administered at multiple doses (at least 3; one dose per animal) and response to GR73632 is measured.

Duration of Action Tests

NK-1 receptor antagonists are administered at multiple pre-treatment times (one administration per animal) including at 0.5, 1, 2, 4, 7, 16, and 24 hours prior to GR73632 injection. GR73632 (Peninsula Labs, CA) is dissolved in saline. Tradipitant is dissolved in 1% CMC/0.5% SLS/0.085% PVP vehicle. CP-122721 and aprepitant are synthesized at Lilly Laboratories and dissolved in 10% ethanol/emulphor and 1% CMC/0.5% SLS/0.085% PVP respectively.

Results

As shown in FIG. 1, orally administered tradipitant potently inhibits NK-1 agonist-induced foot-tapping behavior in gerbils 2 hours after administration of drug in a dose-dependent manner, with an $ED_{50}$ of 0.03±0.004 mg/kg (*$p<0.05$ compared to vehicle for 0.1 mg/kg and 0.3 mg/kg doses). Data shown in FIG. 1 are expressed in number of foot-tapping events occurring in five (5) minutes.

Figure 2:
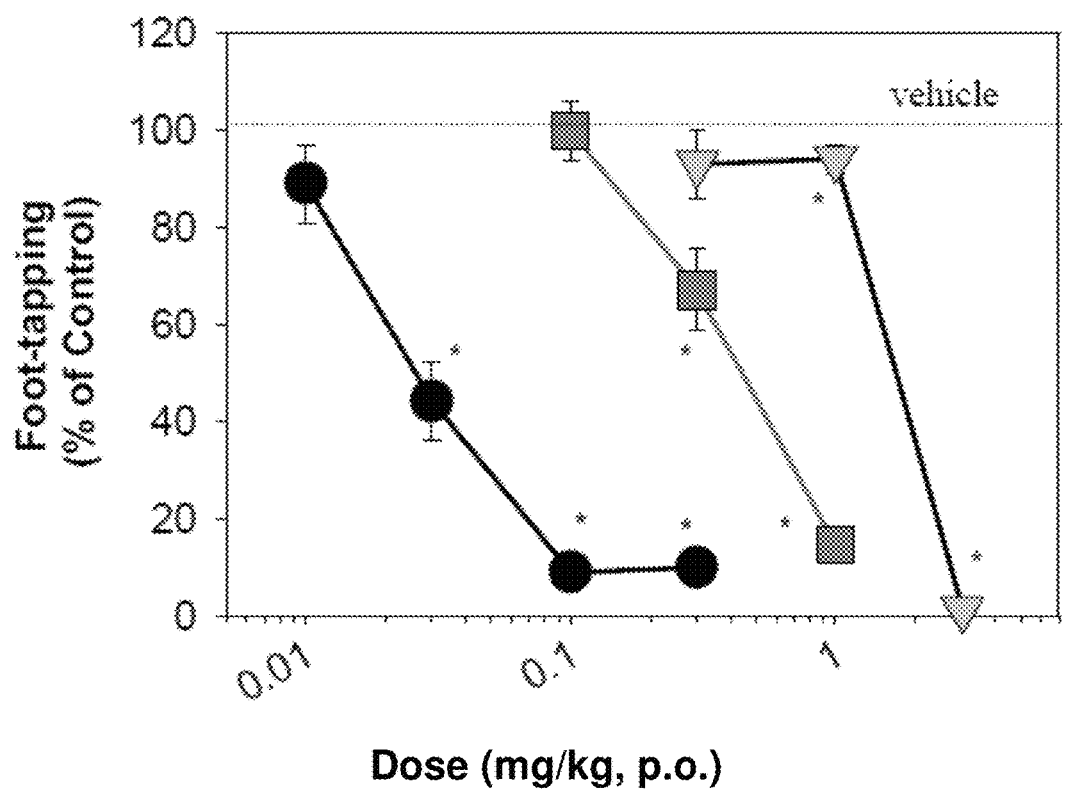
FIG. 2 illustrates the effect of tradipitant on NK-1 agonist (GR73632, 3 pmol, icv)-induced foot-tapping behavior after oral administration: comparison with other NK-1 antagonists, aprepitant and CP-122721: dose response.

FIG. 2 depicts a comparison of the efficacy of tradipitant to that of other NK-1 antagonists, with data expressed as percent control of vehicle (vehicle response to 3 pmol GR73632). Tradipitant is found to be more potent than aprepitant (Merck, $ED_{50}$=0.42 mg/kg±0.05 mg/kg) and CP-122721 (Pfizer, $ED_{50}$=2.2 mg/kg±0.5 mg/kg).

Figure 3:
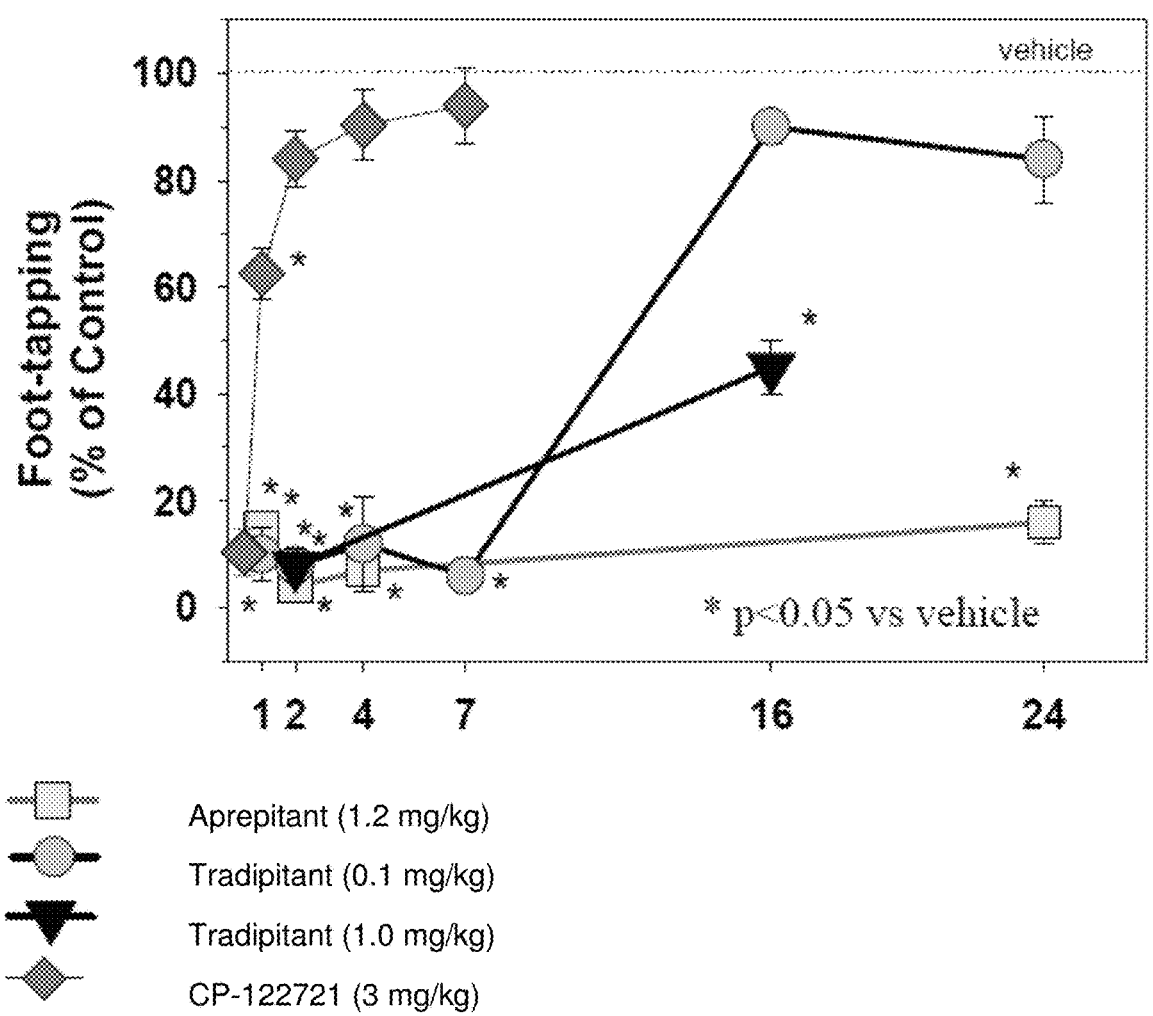
FIG. 3 illustrates the effect of tradipitant on NK-1 agonist (GR73632, 3 pmol, icv)-induced foot-tapping behavior after oral administration: comparison with other NK-1 antagonists, aprepitant and CP-122721: time course.

FIG. 3 depicts the effects of tradipitant over a time course on NK-1 agonist (GR 73632, 3 pmol, icv)-induced foot-tapping behavior after oral administration, compared with that of NK-1 antagonists aprepitant and CP-122721. Tradipitant (0.1 mg/kg, po) is found to significantly inhibit foot-tapping behavior up to 7 hours after administration but the effect is significantly diminished by 16 hours after administration at this dose. However, at a higher dose of 1 mg/kg, tradipitant shows greater than 50% inhibition of foot-tapping behavior 16 hours after administration. The duration of effect of tradipitant is longer than that of CP-122721 (up to 2 hours after administration, 3 mg/kg) while aprepitant (1 mg/kg) shows inhibition of foot-tapping behavior up to 24 hours after administration. Data are expressed as percent control of vehicle (vehicle response to 3 pmol GR73632).

Discussion

The effect of tradipitant on NK-1 agonist-induced foot-tapping behavior in gerbils suggests that tradipitant is a very potent, centrally acting NK-1 receptor antagonist in vivo in the gerbil with a relatively long duration of action.

Example 1.2.2

Emetic Challenge Study in Beagle Dogs with Tradipitant Introduction

Five male dogs are administered a single oral dose of 3 mg/kg aprepitant (a positive control), or tradipitant at 0.3, 1.0, and 3.0 mg/kg in a Latin-square design. An intravenous injection of 0.1 mg/kg apomorphine, a known emetic, is given alone, or 2 hours after administration of tradipitant or aprepitant. Each animal is administered a different dose on a particular dosing day, so that each dose of tradipitant, aprepitant, and apomorphine alone is represented. Over the five (5) weeks of the study, each animal receives each of the treatments, but only one per week. The purpose of this study is to determine if tradipitant suppresses apomorphine-induced emesis.

The low dose of tradipitant is 10 times the $ED_{50}$ in the gerbil foot-tapping model of NK-1 receptor antagonism (Example 1.2.1). The high dose is 100 times this efficacious dose, and is also the dose of aprepitant that has previously been determined to be efficacious against apomorphine-induced emesis in the dog. The mid dose of tradipitant is the approximate half-log interval between the low and high doses.

The oral route of administration is selected for tradipitant because this is the route proposed or currently used clinically. The intravenous route is typically used for experimental apomorphine administration. The beagle dog is considered an effective species for demonstration of antagonism of apomorphine-induced emesis.

Methods

A single oral dose of 0, 0.3, 1.0, or 3.0 mg/kg tradipitant, or 3.0 mg/kg aprepitant is administered to each male dog once a week in gelatin capsules. All animals are dosed over a period of five (5) weeks, with each dog receiving one of five different treatments on each day of dosing. A dose of 0.1 mg/kg apomorphine is administered by intravenous injection approximately two (2) hours after each administration of tradipitant or aprepitant. In cases where apomorphine is administered alone, without prior treatment with tradipitant or aprepitant, apomorphine is given at approximately the same time as when given in combination with tradipitant or aprepitant.

All dogs are fasted overnight prior to each treatment day and then fed approximately one (1) hour after oral dosing (approximately one (1) hour prior to administration of apomorphine). Individual doses are adjusted weekly for changes in body weight.

The dose regimen consists of a 5×5 Latin square design, in which each subject receives 1 dose or dose combination per week (6 day washout) as shown in Table 3 below.

TABLE 3

Latin Square Design

| | Study week 1 | Study week 2 | Study week 3 | Study week 4 | Study week 5 |
|---|---|---|---|---|---|
| Dog 1 | APO + 0.3 mg/kg tradipitant | APO + aprepitant | APO + 3 mg/kg tradipitant | APO | APO + 1 mg/kg tradipitant |
| Dog 2 | APO + aprepitant | APO + 1 mg/kg tradipitant | APO | APO + 0.3 mg/kg tradipitant | APO + 3 mg/kg tradipitant |
| Dog 3 | APO + 3 mg/kg tradipitant | APO | APO + aprepitant | APO + 1 mg/kg tradipitant | APO + 0.3 mg/kg tradipitant |
| Dog 4 | APO | APO + 0.3 mg/kg tradipitant | APO + 1 mg/kg tradipitant | APO + 3 mg/kg tradipitant | APO + aprepitant |
| Dog 5 | APO + 1 mg/kg tradipitant | APO + 3 mg/kg tradipitant | APO + 0.3 mg/kg tradipitant | APO + aprepitant | APO |

The number of emetic episodes is recorded for approximately one hour following the injection of apomorphine, and plasma concentrations at anticipated Tmax of tradipitant (2 hours post-dosing) are evaluated.

Results

Table 4 provides individual and mean and standard deviation values for the 2 hour plasma concentrations of tradipitant. All animals administered tradipitant have measurable levels at 2 hours post-dose. In general, plasma concentrations at 2 hours post-dose increase with increasing dose in a sub-proportional manner. As observed in other studies in dogs, the exposure to tradipitant is variable between animals. Individual animal data reveal no relationship between plasma concentrations and week of administration.

TABLE 4

Plasma concentrations of tradipitant (ng/ml)

| Administered Dose | 0.3 mg/kg Concentration of tradipitant (ng/ml) | 1.0 mg/kg Concentration of tradipitant (ng/ml) | 3.0 mg/kg Concentration of tradipitant (ng/ml) |
|---|---|---|---|
| Dog 1 | 51.20 | 175.58 | 122.73 |
| Dog 2 | 41.33 | 86.49 | 256.58 |
| Dog 3 | 90.93 | 240.84 | 316.20 |
| Dog 4 | 83.38 | 100.97 | 682.91 |
| Dog 5 | 22.59 | 61.56 | 119.79 |
| Mean (SD) | 57.89 (28.75) | 133.09 (73.71) | 299.64 (230.58) |

As shown in Table 5, emesis occurs after each treatment, with the largest incidence of emesis occurring in the apomorphine alone group. One dog (Dog 3) has a single episode of emesis at each dose of tradipitant and aprepitant; this dog also has the greatest number of emetic episodes with apomorphine alone (12). No emesis occurs in the remaining four (4) dogs at any dose of tradipitant or aprepitant. These dogs have an average of four (4) emetic episodes with apomorphine alone. The antiemetic effect of aprepitant supports the validity of this model.

TABLE 5

Emetic episodes by treatment group

| Test article* | Dose level (mg/kg) | Total No. Emetic Episodes |
|---|---|---|
| APO (control) | 0 | 28 |
| aprepitant | 3.0 | 1** |
| tradipitant | 0.3 | 1** |
| tradipitant | 1.0 | 1** |
| tradipitant | 3.0 | 1** |

*Apomorphine is administered as a challenge dose to all groups.
**All episodes occur in same dog (Dog 3).

Results of this study indicate that tradipitant is effective against apomorphine-induced emesis at each dose tested (0.3, 1.0, and 3.0 mg/kg).

Example 1.2.3

Tradipitant Inhibits Substance P-Induced Vocalization in Guinea Pigs

Introduction

When introduced into the brain, the NK-1 receptor agonist substance P (SP) elicits distress vocalizations in the guinea pig that can be inhibited by NK-1 antagonists.

This behavioral assay is used to demonstrate potency and CNS penetration of NK-1 antagonists in the guinea pig, a species that has receptor affinity for NK-1 antagonists that is similar to humans.

Methods

Figure 5:
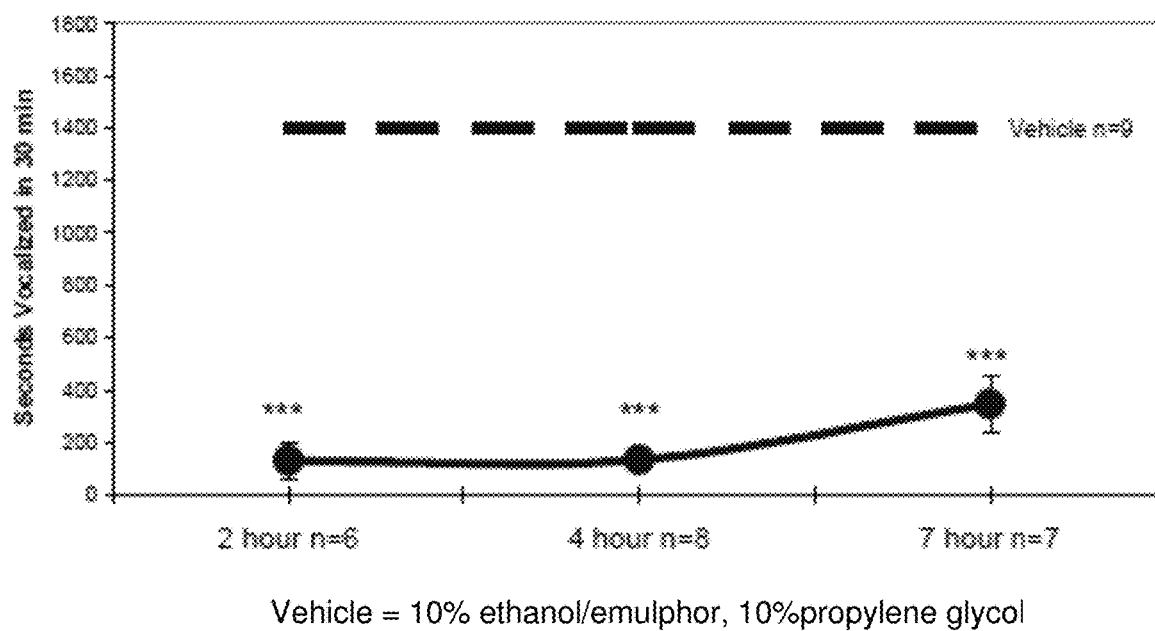
FIG. 5 illustrates the duration of activity, i.e. suppression of NK-1 agonist-induced vocalization in guinea pigs, following a 0.1 mg/kg dose of tradipitant.
Figure 6:
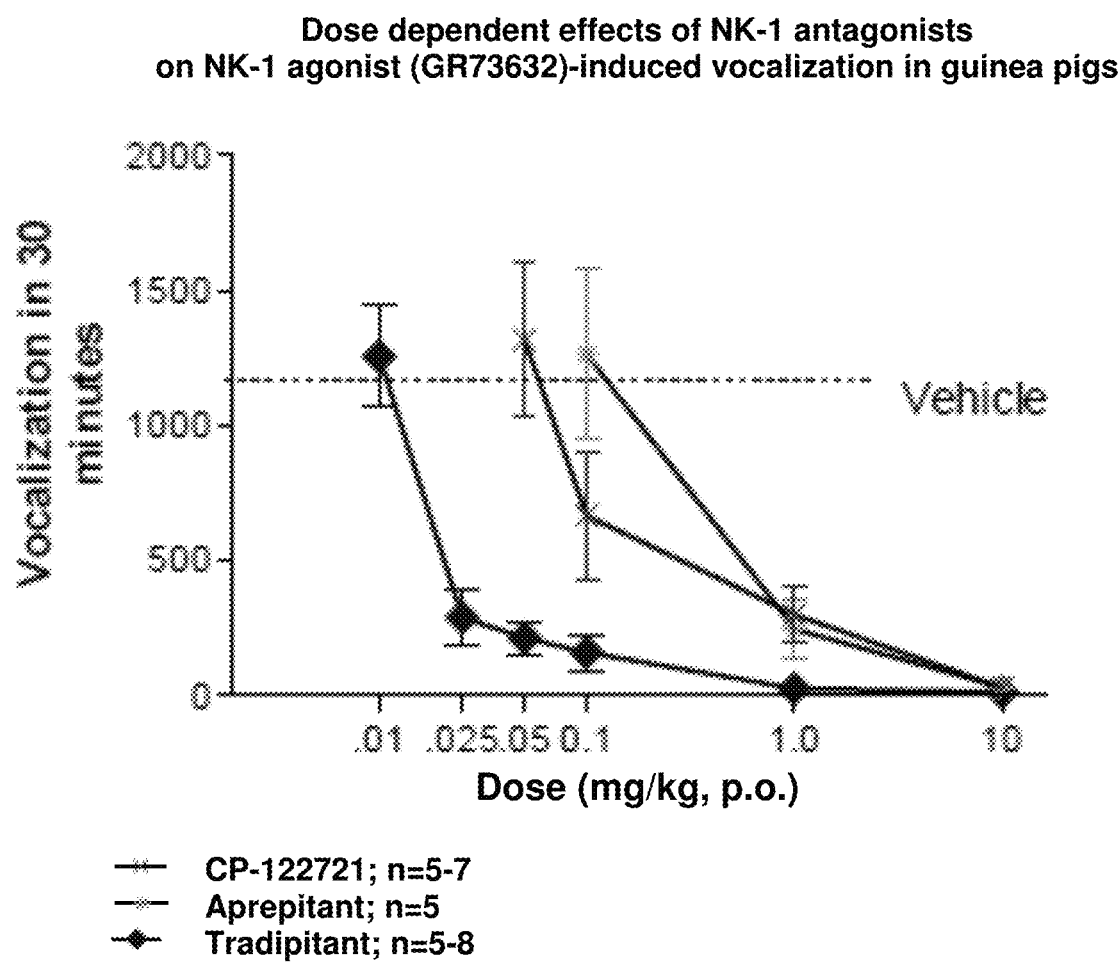
FIG. 6 illustrates the dose-dependent effects of tradipitant, and the effects of various NK-1 antagonists in the guinea pig vocalization assay.

Male Dunkin/Hartley guinea pigs (200 to 250 grams) are orally administered either vehicle or an NK-1 antagonist. Approximately 45 minutes later (for dose response studies), the animals are anesthetized and 0.1 nmol of GR73632 (SP analog) in a vehicle volume of 5 μl is injected into the cerebral ventricle at the intersection of bregma and the midline of the skull. Animals are placed in a dark testing chamber located inside of a sound attenuation cubicle and vocalizations are recorded for 30 minutes following recovery from anesthesia. The time spent vocalizing is quantified for each animal. In the duration of action study, 0.1 mg/kg of tradipitant or vehicle solution is administered orally and then 2, 4, or 7 hours later, 0.1 nmol of GR73632 is administered into the cerebral ventricle as described above. Vocalizations are recorded and quantified as indicated above. Vehicle solutions are either CMC (FIG. 4 data) or an ethanol/emulphor solution (FIGS. 5 and 6). Data is analyzed using one-tailed t-tests.

Results

Figure 4:
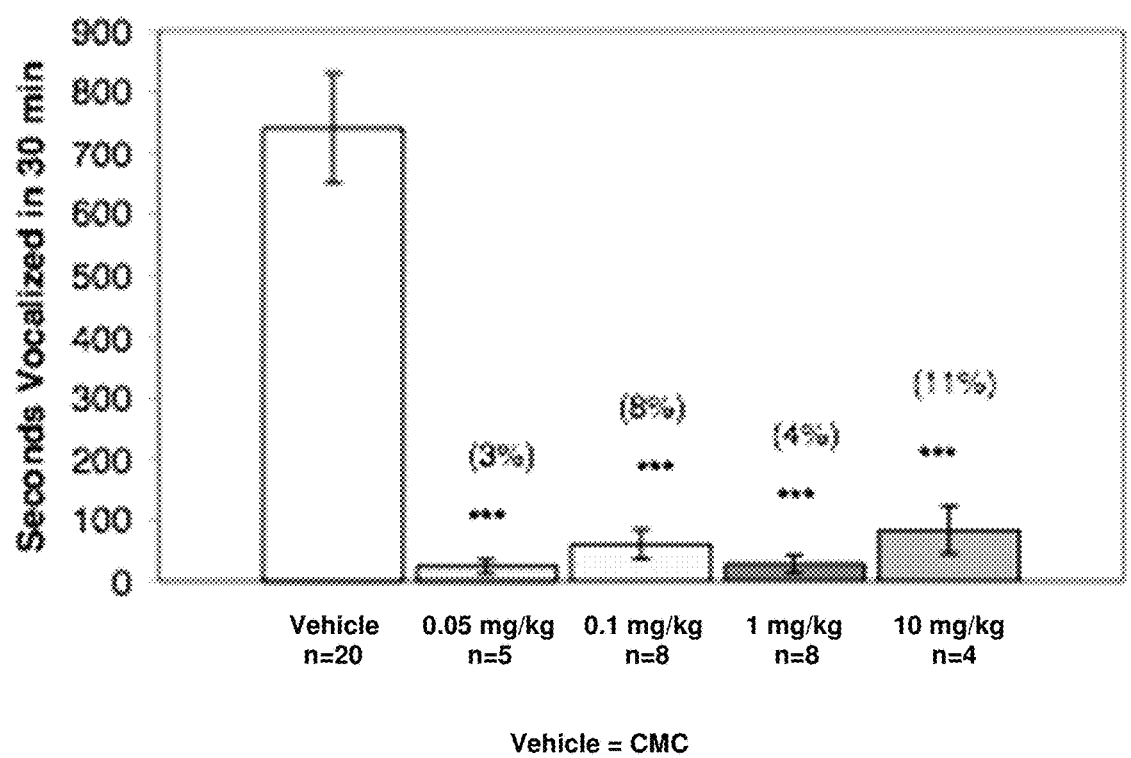
FIG. 4 illustrates the effect of tradipitant on GR73632-induced vocalization in guinea pigs across a concentration range of 0.05 to 10 mg/kg.

As shown in FIG. 4, oral administration of tradipitant produces significant inhibition of agonist-induced vocalization at doses of 10 mg/kg ($p<0.001$), 1.0 mg/kg ($p<0.001$), 0.1 mg/kg ($p<0.001$), and 0.05 mg/kg ($p<0.001$). Data shown parenthetically in FIG. 4 indicate percent of control response. Activity of tradipitant does not wane at the lower doses, indicating that even lower doses would be required to produce a dose response function.

As shown in FIG. 5, the effect of 0.1 mg/kg tradipitant is significantly active in suppressing agonist-induced vocalization at 7 hours following oral administration of the antagonist compound.

A second dose-response study compares potencies of tradipitant, aprepitant, and CP-122721. As shown in FIG. 6, all NK-1 antagonists tested produce significant inhibition of vocalization at 1 mg/kg. Only tradipitant retains significant inhibitory activity at and below 0.1 mg/kg. The minimum effective dose of tradipitant is found to be 0.025 mg/kg which produces highly significant (p<0.001) inhibition of vocalization compared to controls. (Vehicle was ethanol/emulphor; vehicle groups were n=5-14 per compound.)

Discussion

Tradipitant significantly inhibits NK-1 agonist-induced vocalization in guinea pigs, indicating that this compound is an orally available and brain-penetrant NK-1 antagonist. The minimum effective dose (MED) that produces this effect is 0.025 mg/kg. Tradipitant, administered orally, is shown to have a duration of activity that exceeds 7 hours. In this experimental paradigm, tradipitant is substantially more potent than aprepitant and CP-122721.

Example 1.2.4

Occupancy of NK-1 Receptors

A tracer NK-1 antagonist compound (GR205171) is used to evaluate the ability of other NK-1 antagonists to occupy the brain NK-1 receptors. In these studies, the test compounds are administered orally and the tracer compound is administered intravenously afterward. The occupancy of the NK-1 receptors is evaluated by quantitating the amount of the tracer compound bound to the brain NK-1 receptors after increasing doses of the test compounds. Using this paradigm, tradipitant has an estimated $ED_{50}$ of 0.04 mg/kg p.o. and is substantially more potent than the other antagonists evaluated.

Example 2

Clinical Study of Gastrointestinal Motility

A single-center, randomized, double-blind, placebo-controlled study is conducted to investigate the effect of tradipitant on small bowel transit time. A total of 15 healthy subjects, including 12 men and 3 women between the ages of 19 and 63 years, are enrolled in the study and receive at least 1 dose of study medication. A total of 13 subjects complete the study. Subjects are randomized to receive 20 mg of tradipitant, 200 mg of tradipitant, or placebo as a single oral dose within each of 3 periods, co-administered with a capsule radiolabeled with a maximum of 1MBq $^{111}$In. Four hours post-dose, all subjects also receive a second capsule radiolabeled with a maximum of 4MBq $^{99}$mTc. Each subject receives all 3 doses during the study. For all dosing regimens, in vivo gamma scintigraphic studies are performed at predetermined intervals, and the following scintigraphic parameters are analyzed: onset and completion of gastric emptying, onset and completion of colon arrival, initiation and completion of small bowel transit, and initial and complete disintegration of the capsule (anatomical location and time).

A statistically significant effect of tradipitant on small bowel transit time is observed in the study. No effect on gastric emptying is observed in this study. However, the study is underpowered with respect to this parameter.

Example 3

Motion Sickness Prevention

A randomized, double blind, placebo-controlled clinical study of motion sickness is conducted, in which 126 human subjects ("study participants"), each having a prior history of motion sickness, are subjected to sea travel in the Pacific Ocean under varied weather conditions.

Methods

Study participants are distributed over seven boat trips off the coast of Los Angeles, Calif., USA. For each trip, sea conditions and participant self-evaluation of symptoms of motion sickness are recorded. Among the seven trips, three are under "rough" sea conditions, conducive to producing motion sickness with wave heights above one meter. The remaining four trips are made under "calm" conditions, with wave heights less than one meter, and are less likely to produce motion sickness. Under "rough" sea conditions, 72.2% of the placebo treated patients experience vomiting compared to only 26.7% under "calm" conditions.

Subjects are randomized to receive either tradipitant 170 mg or placebo by mouth in a blinded fashion, prior to travel initiation. Participants report their symptoms at predetermined time intervals during the travel period. Primary end points of the study include: percentage of participants vomiting, and Motion Sickness Severity Scale (MSSS) Worst score. The MSSS is a 7 point scale ranging from 0 ("no symptoms") to 6 ("vomiting"). An exploratory analysis is also performed to evaluate the effects of tradipitant under "calm" and "rough" seas.

Results

Results are reported in Table 6 below. In the overall intent to treat (ITT) population (n=126), a significantly higher percentage of participants experience vomiting in the placebo arm of the study (39.7%) as compared to the tradipitant arm (17.5%), p value=0.0039. The MSSS Worst score endpoint also favors tradipitant (3.4) vs. placebo (3.75), although the difference does not reach statistical significance, p value=0.293. Under "calm" sea conditions, only a small percentage of participants in either arm experience vomiting, 26.7% in the placebo arm and 18.2% in the tradipitant treatment arm (not significant). A similar MSSS Worst score is seen between the two groups under "calm" conditions, 3.32 (placebo arm) and 3.40 (tradipitant treatment arm) (not statistically significant). Under "rough" sea conditions, 72.2% of the placebo treated patients vomit as compared to 15.8% of those treated with tradipitant, p value=0.0009. A significant effect is also seen under "rough" conditions in the MSSS Worst score, 4.57 (placebo) and 3.19 (tradipitant), p value=0.0235.

TABLE 6

Results for the Overall population and for the Calm and Rough Sea sub-populations.

| | | Tradipitant | Placebo | Difference | P-value |
|---|---|---|---|---|---|
| ITT* | | n = 63 | n = 63 | | |
| % Vomiting | | 17.5% | 39.7% | 22.2% | 0.0039 |
| Worst MSSS | | 3.40 | 3.75 | 0.35 | 0.2936 |
| | Calm Sea | n = 44 | n = 45 | | |
| % Vomiting | | 18.2% | 26.7% | 8.5% | 0.3123 |
| Worst MSSS | | 3.4 | 3.32 | −0.09 | 0.8271 |
| | Rough Sea | n = 19 | n = 18 | | |
| % Vomiting | | 15.8% | 72.2% | 56.4% | 0.0009 |
| Worst MSSS | | 3.19 | 4.57 | 1.38 | 0.0235 |

Conclusions

The foregoing data show that treatment with 170 mg tradipitant by mouth prior to travel initiation provides a significant reduction in the incidence of vomiting and in MSSS Worst score during travel under rough sea conditions and in overall conditions, as well as modest (not statistically significant) reductions during travel under calm conditions.

These findings show that tradipitant at a dose of 170 mg provides an effective treatment for motion sickness.

EMBODIMENTS

In addition to other illustrative embodiments, this invention can be seen to comprise one or more of the following illustrative embodiments:

1. A method of treating a subject about to engage in an activity involving sickness-inducing motion comprising: administering tradipitant to said subject, prior to the commencement of said activity, in an amount effective to prevent motion sickness or at least one symptom of motion sickness in said subject.

2. The method of embodiment 1, wherein said activity is vehicle travel.

3. The method of either of embodiments 1 or 2, wherein said administration occurs about 30 minutes prior to entering a vehicle.

4. The method of either of embodiments 1 or 2, wherein the administration occurs about 30 minutes prior to commencement of vehicle travel.

5. A method of treating a subject with motion sickness or at least one symptom of motion sickness, comprising: administering tradipitant to said subject in an amount effective to treat said sickness or a symptom thereof.

6. The method of any of embodiments 1-5, wherein the effective amount is 100-400 mg.

7. The method of any of embodiments 1-5, wherein the effective amount is 100-300 mg.

8. The method of any of embodiments 1-5, wherein the effective amount is 100-200 mg.

9. The method of any of embodiments 1-5, wherein the effective amount is about 170 mg.

10. The method of any preceding embodiment, wherein the administration further comprises oral administration of the effective amount of tradipitant.

11. The method of embodiment 10, wherein the tradipitant administered to the subject is in a solid immediate release form such as a capsule or tablet comprising tradipitant and one or more pharmaceutically acceptable excipients.

12. The method of any one of embodiments 2-4, wherein the vehicle travel is via automobile, airplane, helicopter, boat, train, bus, or other vehicle.

13. The method of any preceding embodiment, wherein the at least one symptom is nausea, vomiting, dizziness, headache, fullness, or disorientation.

14. Tradipitant for use in any of the preceding methods of treatment.

15. A pharmaceutical composition comprising tradipitant for use in any of the preceding methods.

16. Tradipitant for use in the manufacture of a pharmaceutical composition comprising tradipitant for use in any of the preceding methods.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mg, or, more specifically, about 5 mg to about 20 mg," is inclusive of the endpoints and all intermediate values of the ranges of "about 5 mg to about 25 mg," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method of treating a subject about to engage in an activity involving sickness-inducing motion consisting essentially of:
   administering tradipitant to said subject, prior to the commencement of said activity, in an amount effective to prevent motion sickness or at least one symptom of motion sickness in said subject.

2. The method of claim 1, wherein said activity is vehicle travel.

3. The method of claim 2, wherein said administration occurs about 30 minutes prior to entering a vehicle.

4. The method of claim 2, wherein said administration occurs about 30 minutes prior to commencement of vehicle travel.

5. The method of claim 1, wherein said effective amount is 100-400 mg.

6. The method of claim 5, wherein said effective amount is 100-300 mg.

7. The method of claim 6, wherein said effective amount is 100-200 mg.

8. The method of claim 7, wherein said effective amount is about 170 mg.

9. The method of claim 1, wherein the administering further comprises orally administering an effective amount of tradipitant.

10. The method of claim 9, wherein said tradipitant is orally administered in a solid immediate release form the solid immediate release form being a capsule or tablet.

11. The method of claim 2, wherein said vehicle travel is via automobile, airplane, helicopter, boat, train, or bus.

12. The method of claim 1, wherein said at least one symptom is nausea, vomiting, dizziness, headache, fullness, or disorientation.

13. A method of treating a subject with motion sickness or at least one symptom of motion sickness, consisting essentially of:
   administering tradipitant to said subject in an amount effective to treat said sickness or a symptom thereof.

14. The method of claim 13, wherein said effective amount is 100-400 mg.

15. The method of claim 14, wherein said effective amount is 100-300 mg.

16. The method of claim 15, wherein said effective amount is 100-200 mg.

17. The method of claim 16, wherein said effective amount is about 170 mg.

18. The method of claim 13, wherein said administration further comprises oral administration of tradipitant.

19. The method of claim 18, wherein said tradipitant is orally administered in a solid immediate release form the solid immediate release form being a capsule or tablet.

20. The method of claim 13, wherein said at least one symptom is nausea, vomiting, dizziness, headache, fullness, or disorientation.

* * * * *